United States Patent
Grunlan et al.

(10) Patent No.: US 10,624,987 B2
(45) Date of Patent: Apr. 21, 2020

(54) IMPLANT-BASED REPAIR OF OSTEOCHONDRAL DEFECTS

(71) Applicant: The Texas A&M University System, College Station, TX (US)

(72) Inventors: Melissa A. Grunlan, College Station, TX (US); Mariah S. Hahn, Ballston Lake, NY (US); William B. Saunders, College Station, TX (US)

(73) Assignee: The Texas A&M University System, College Station, TX (US)

( * ) Notice: Subject to any disclaimer, the term of this patent is extended or adjusted under 35 U.S.C. 154(b) by 37 days.

(21) Appl. No.: 15/757,361

(22) PCT Filed: Sep. 3, 2016

(86) PCT No.: PCT/US2016/050310
§ 371 (c)(1),
(2) Date: Mar. 3, 2018

(87) PCT Pub. No.: WO2017/041068
PCT Pub. Date: Mar. 9, 2017

(65) Prior Publication Data
US 2018/0236128 A1   Aug. 23, 2018

Related U.S. Application Data

(60) Provisional application No. 62/213,962, filed on Sep. 3, 2015.

(51) Int. Cl.
*A61L 2/16* (2006.01)
*A61L 27/16* (2006.01)
(Continued)

(52) U.S. Cl.
CPC .......... *A61L 27/16* (2013.01); *A61F 2/30756* (2013.01); *A61F 2/30767* (2013.01);
(Continued)

(58) Field of Classification Search
CPC .... A61L 27/18; A61L 27/56; A61L 2300/412; A61L 2420/04; A61L 2420/08;
(Continued)

(56) References Cited

U.S. PATENT DOCUMENTS

| | | |
|---|---|---|
| 2005/0043813 A1 | 2/2005 | Kusanagi et al. |
| 2006/0239986 A1 | 10/2006 | Perez-Luna et al. |

(Continued)

OTHER PUBLICATIONS

Kizilel, S. et al., "Sequential formation of covalently bonded hydrogel multilayers through surface initiated photopolymerization", Biomaterials, vol. 27 issue 8, Sep. 12, 2005, pp. 1209-1215.
(Continued)

*Primary Examiner* — Ernst V Arnold
(74) *Attorney, Agent, or Firm* — Winstead PC

(57) ABSTRACT

The present invention is directed to a unique technology for preparing a growth-factor free, cylindrical, hydrogel implant that has multiple (three or more) longitudinal hydrogel zones with varying chemical and physical properties. The implant may be wholly made of hydrogels or the hydrogels may be associated with cells, such as mesenchymal stem cells (MSCs).

20 Claims, 4 Drawing Sheets

(51) Int. Cl.
*A61L 27/18* (2006.01)
*A61F 2/30* (2006.01)
*A61L 27/52* (2006.01)
*A61L 27/54* (2006.01)
*A61L 27/56* (2006.01)

(52) U.S. Cl.
CPC .............. *A61L 27/18* (2013.01); *A61L 27/52* (2013.01); *A61L 27/54* (2013.01); *A61L 27/56* (2013.01); *A61F 2/3094* (2013.01); *A61F 2002/30011* (2013.01); *A61F 2002/30075* (2013.01); *A61F 2002/30224* (2013.01); *A61F 2002/30766* (2013.01); *A61L 2300/412* (2013.01); *A61L 2420/04* (2013.01); *A61L 2420/08* (2013.01); *A61L 2430/02* (2013.01); *A61L 2430/06* (2013.01)

(58) Field of Classification Search
CPC .. A61L 2430/02; A61L 2430/06; A61L 27/16; A61L 27/52; A61L 27/54; C08L 71/02; C08L 83/04; A61F 2002/30011; A61F 2002/30075; A61F 2002/30224; A61F 2002/30766; A61F 2/30756; A61F 2/30767; A61F 2/3094
See application file for complete search history.

(56) References Cited

U.S. PATENT DOCUMENTS

2010/0204800 A1* 8/2010 Thomas ................. A61L 27/52
 623/19.11
2011/0008442 A1 1/2011 Zawko et al.

OTHER PUBLICATIONS

Munoz-Pinto, D. J. et al., Osteogenic Potential of Poly(Ethylene Glycol)-Poly(Dimethylsiloxane) Hybrid Hydrogels, Tissue Engineering: Part A, vol. 18, Nos. 15 and 16, May 31, 2012, pp. 1710-1719.

Hou, Y. et al., "Photo-Cross-Linked PDMSstar-PEG Hydrogels: Synthesis, Characterization, and Potential Application for Tissue Engineering Scaffolds", Biomacromolecules, vol. 11 issue 3, Feb. 10, 2010, pp. 648-656.

* cited by examiner

IMPLANT-BASED REPAIR OF OSTEOCHONDRAL DEFECTS

CROSS-REFERENCE TO RELATED APPLICATIONS

This application claims the benefit of U.S. Provisional Patent Application Ser. No. 62/213,962, filed on Sep. 3, 2015, which is incorporated herein by reference in its entirety.

STATEMENT REGARDING FEDERALLY SPONSORED RESEARCH AND DEVELOPMENT

This invention was made with government support under Grant No. 1R03EB015202 and Grant No. 1R21HL089964-01 awarded by the National Institutes of Health. The government has certain rights in the invention.

BACKGROUND OF THE INVENTION

Osteochondral defects present significant challenges for treatment in animals and humans. Osteochondral tissues are complex due to the gradual transition from cartilage to bone tissue types. The nature of the osteochondral tissue is important to its mechanical functionality and integrity. Healing of all tissues to recapitulate the native osteochondral tissue is the optimal treatment outcome. However, there is currently no available method of repairing all the tissues using a single implantable scaffold. A scaffold, by nature of its chemical and physical properties, can guide associated cells to produce the desired tissue. However, hydrogel scaffolds are generally prepared with a "single" composition, and hence, display a single set of chemical and physical properties. A hydrogel scaffold for osteochondral healing should present spatially varied properties in order to induce healing of specific tissue or tissues in a given region. In efforts to overcome this limitation, two or more different scaffolds may be joined in some fashion following fabrication of the individual hydrogels. However, this produces a "hard interface" (i.e. lacking a gradual transition) between the different hydrogels which can lead to mechanical failure. Therefore, the use of hydrogels as implanted scaffolds in treating osteochondral defects has been met with limited success. There is clearly a need to identify hydrogel scaffold compositions and their preparation methods which provide spatially varied properties and soft interfaces between different regions leading to the efficient healing of each of the various tissue types within the osteochondral defect.

SUMMARY OF THE INVENTION

The present invention is directed to a unique technology for preparing a growth-factor free, cylindrical, hydrogel implant that has multiple (three or more) longitudinal hydrogel zones with varying chemical and physical properties. The implant may be wholly made of hydrogels or the hydrogels may be associated with cells, such as mesenchymal stem cells (MSCs). The varying chemical and physical properties of each longitudinal hydrogel zone have the ability to permit migration throughout the implant, to direct the associated cells to differentiate and expand their population, and to integrate into the proximate osteochondral tissues. The implant is prepared in such a way that the longitudinal hydrogel zones are all non-porated, all porated or a combination of both. The implant is also prepared as a cylindrical, monolithic implant in which zones are formed in series with a soft interface (i.e. gradual transition or interpenetration between zones) to better recapitulate the native osteonchondal tissue and to avoid mechanical failure.

DETAILED DESCRIPTION OF THE INVENTION

In an embodiment of the invention, a poragen template is a template over which the hydrogel implant may be cast. Casting the hydrogel implant over the poragen template will result in pores forming within the hydrogel implant. The poragen may be salt (e.g. NaCl, $CaCl_2$, $RbCl_2$), sugar, paraffin or other particles. It is understood within the field of art that non-porated hydrogel zones will contain pores which are inherently present, based upon the nature of the hydrogel comprising the hydrogel zone. In this application, the term "non-porated" indicates that the pores are not being defined nor enlarged nor are the number of pores being increased, intentionally in a hydrogel zone via the use of a poragen template or other methods, above that which is inherently present following formation of the hydrogel zone. In addition, the term "porated" indicates that a pore size or pore size distribution was defined by use of a poragen during fabrication of the hydrogel zone.

Each individual longitudinal hydrogel zone may be of varying length, and the length of each hydrogel zone would ideally parallel that of the adjacent native osteochondral tissue. Thus the length of each hydrogel zone will depend upon the thickness of the tissue that it spans. The hydrogel zones may be discrete layers or continuous gradients of different compositions. Between zones, some degree of interpenetration exists to integrate the zones and create soft interfaces. The implant may be a hydrogel comprised of a hydrophobic, inorganic polymer(s), within an organic polymer(s), distributed in spatially varied concentrations among hydrogel zones. Hydrogel zones with increasingly higher levels of inorganic polymer may generally be placed proximately to adjacent tissue regions with corresponding increasing osseous (i.e. bone-like) character.

Figure 1:
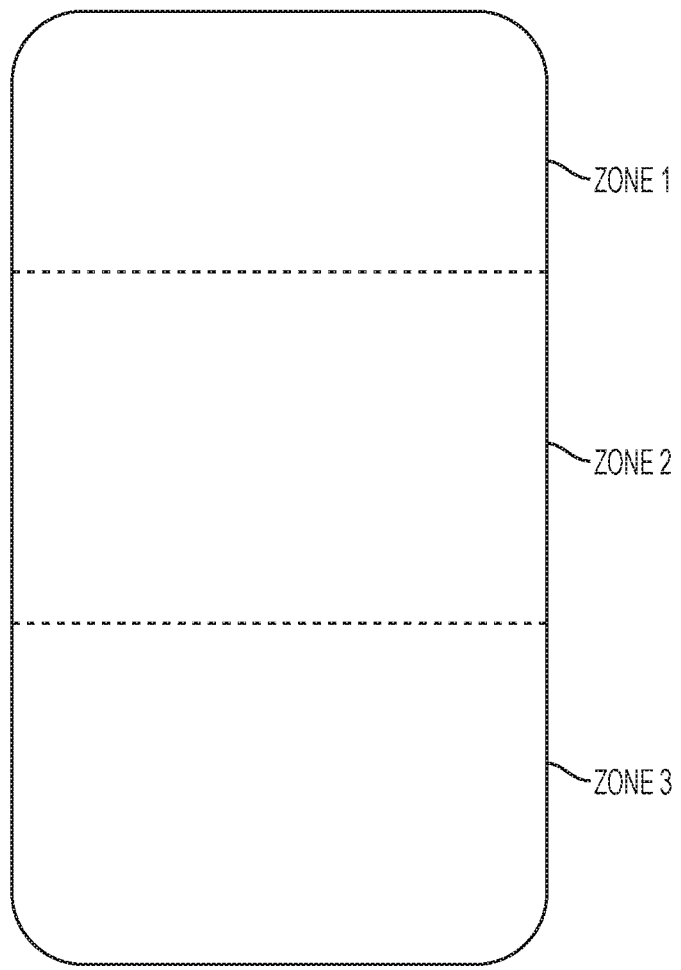
FIG. 1 shows a hydrogel implant comprised of 3 non-porated hydrogel zones in accordance with an embodiment of the claimed invention.

Due to its cylindrical geometry (i.e. resembling autograft "plugs"), the hydrogel implant may be placed within the osteochondral defect using conventional or arthroscopic surgery. Insertion of the implant is expected to occur by placement into a pre-drilled hole or holes formed in the defect site (i.e. where tissue damage has occurred). It is anticipated that a single implant would be inserted into a single pre-drilled holed. The individual implant may be prepared with essentially any size length and any size diameter, such that the implant could fit within the pre-drilled hole dimensions. This property (tunable length and diameter as well as corresponding zone lengths) allows for treatment of multiple animal species with varying sizes of osteochondral defects. Moreover, the composition of a given implant can be readily varied based on the defect size, animal species and desired cell behavior necessary for healing the various tissues. Alternatively, multiple implants of the same or different size may be inserted into a single pre-drilled hole. In FIG. 1, a schematic drawing of a hydrogel implant with three zones is provided. Here, the zones (Zone 1, Zone 2 and Zone 3) are depicted as having similar thicknesses. In practice, the zone thicknesses may be prepared to parallel the thicknesses of the different tissue types of the native osteochondral defect (e.g. cartilage layer, transition zone, subchondral bone region and cancellous bone region). However, each zone within a hydrogel implant may have different porosity from the other zones, as in FIGS. 2 and 3. Preparation of the hydrogel implant may be done using cylindrical glass chambers (i.e. molds) that have an inner diameter which may roughly correspond to the diameter of the pre-drilled hole(s) of the osteochondral defect. The method of preparation allows the production of three or more longitudinal hydrogel zones with varying chemical or physical properties in such a way that the hydrogel zones interpenetrate within their boundaries.

Figure 2:
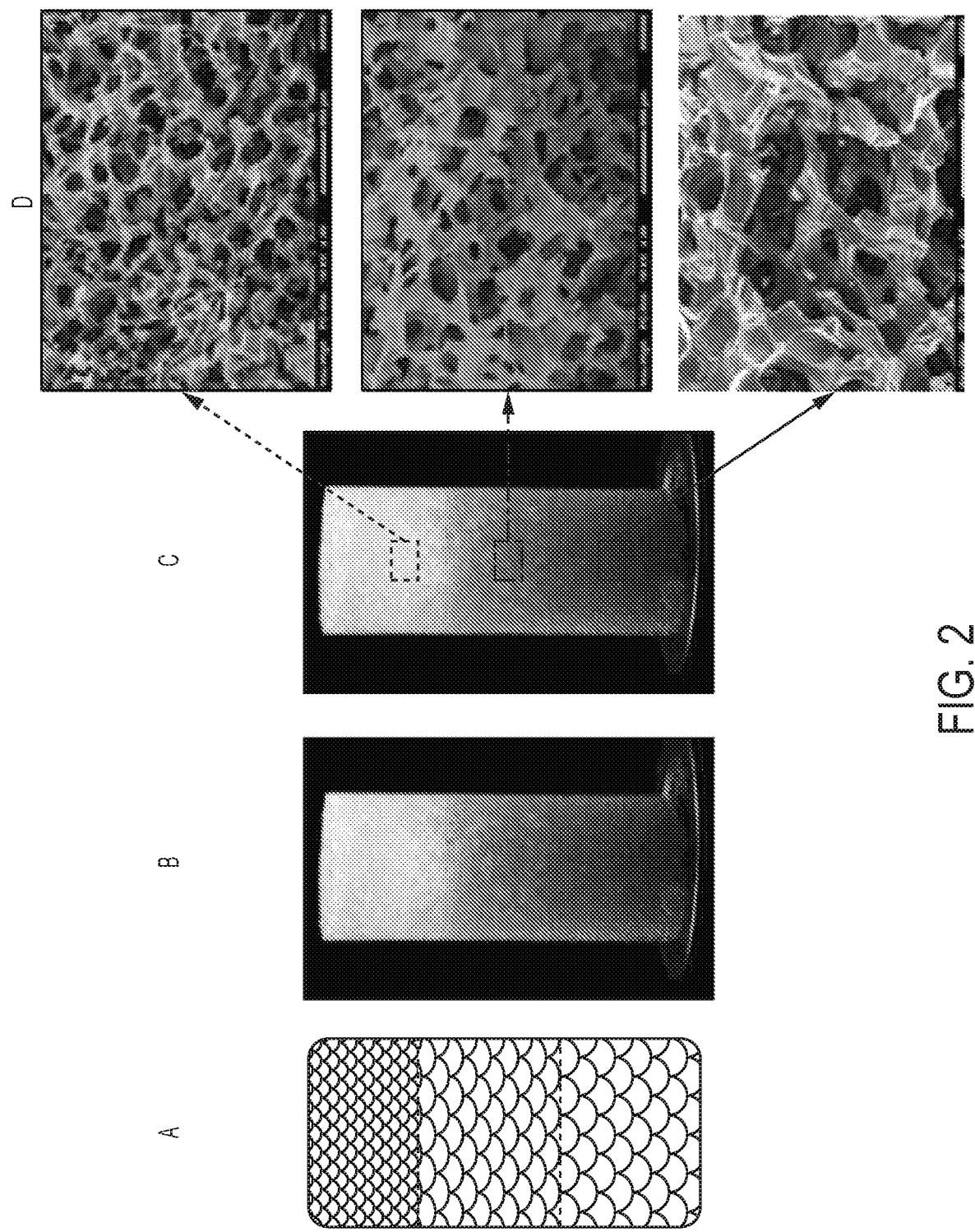
FIG. 2 shows a hydrogel implant comprised of 3 porated hydrogel zones of different pore sizes in accordance with an embodiment of the invention.

In FIG. 2, the zones are depicted as being prepared having similar thicknesses. In practice, the zone thicknesses may be prepared to parallel the thicknesses of the different tissue types of the native osteochondral defect (e.g. cartilage layer, transition zone, subchondral bone region and cancellous bone region). FIG. 2A shows a schematic depiction of an implant, FIG. 2B shows a hydrogel implant, FIG. 2C shows hydrogel implant and correspond scanning electron microscopy (SEM) images (FIG. 2D) showing different pore sizes of each zone. FIGS. 2B and 2C are examples of hydrogel implants, with three zones of varying porosity, which have been removed from a casting cylinder and the salt template leached (i.e. dissolved) out of the implant by soaking in water. This method of preparation avoids the problem of a hard interface between the hydrogel zones, which can lead to mechanical failure. In addition, the interpenetration of the hydrogel zones recapitulates the gradual transition of native osteochondral tissues. Porated zones may be prepared using a solvent-casting, poragen leaching method. The solvent-casting may be done using an organic, an aqueous, or solvent mixture thereof in which the polymer(s), macromere(s), monomer(s), crosslinker(s), initiator(s) and/or catalyst(s) are dissolved or dispersed. This "precursor solution" is then cast over the salt template contained within the glass chamber. The salt may be sodium chloride or any salt or other poragen which may be subsequently dissolved (i.e. leached) or removed in some way from the hydrogel. The poragen template may first be "fused" (for example by treatment with water) such that the resulting pores are better interconnected. Centrifugation of the poragen template can be used to improve packing, fusion and/or distribution of precursor solution in the template. The hydrogel is then formed via physically or chemically cure (i.e. crosslinking) and this process may be accelerated with UV-light, heat, or other methods. The poragen is then removed from the hydrogel by placing in an aqueous solution such as water. It is anticipated that a single hydrogel implant would be formed one zone at a time with poragen leaching occurring after all zones have been formed. However, the sequence of steps may be performed in other ways. The diameter of the salt used for a particular zone will establish the final pore size of the hydrogel. Non-porated hydrogel zones are likewise produced but without the use of a poragen. FIG. 2D shows a magnified view of the three zoned porated hydrogel implant in FIG. 2C, and the variations in porosity for each zone. The uppermost panel of the top zone in FIG. 2D shows smaller pores within the hydrogel zone than in the middle panel displaying the middle zone, in FIG. 2D. The middle panel in FIG. 2D shows smaller pores in the middle zone than those in the bottom panel of FIG. 2D which shows the bottom zone.

Figure 3:
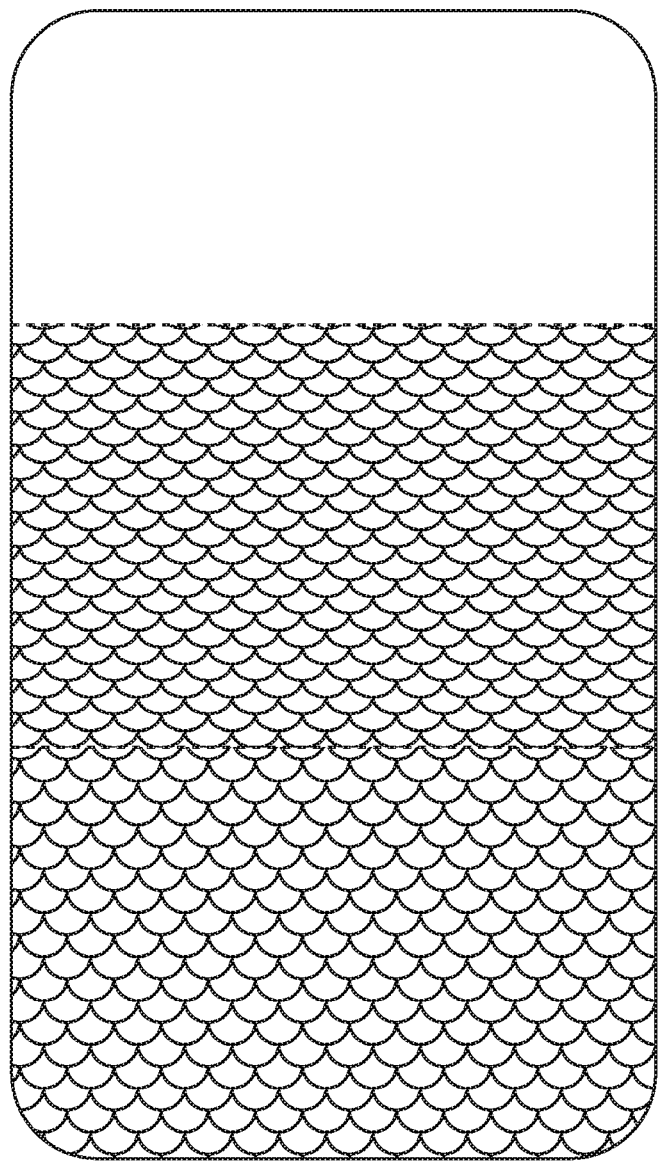
FIG. 3 shows a hydrogel implant comprised of 2 porated hydrogel zones of different pore sizes and 1 non-porated hydrogel zone in accordance with an embodiment of the invention.

FIG. 3 shows a hydrogel implant with three zones, where the top zone is non-porated and the bottom two zones have varying porosity. Here, the zones are depicted as having similar thicknesses. In practice, the zone thicknesses may be prepared to parallel the thicknesses of the different tissue types of the native osteochondral defect (e.g. cartilage layer, transition zone, subchondral bone region and cancellous bone region). Both, the middle and bottom zones are porated—the bottom zone containing larger pores than the middle zone. Thus, this method allows for individual hydrogel zones to be prepared with varying cylindrical dimensions (i.e. diameter and overall length), longitudinal lengths of zones, chemical composition, physical properties (e.g. modulus), number of pores, size of pores, and incorporation of cells. Furthermore, cells may be incorporated into the hydrogel implant during formation of the hydrogel or seeded after fabrication of the hydrogel. For non-porated zones as well as porated zones prepared with an aqueous precursor solution, cells may be "encapsulated" during hydrogel curing or "seeded" after the hydrogel has been formed (and, in the case of porated hydrogel zones, the poragen has been removed). Following insertion into the osteochondral defect, cells from adjacent tissues may also migrate into the hydrogel implant.

Alternately, these implants may be prepared in a non-cylindrical chamber. Subsequent to the hydrogel zones curing, a cylindrical shaped implant may be prepared by cutting a cylindrical implant using a die punch, either by hand or by a machine.

Figure 4:
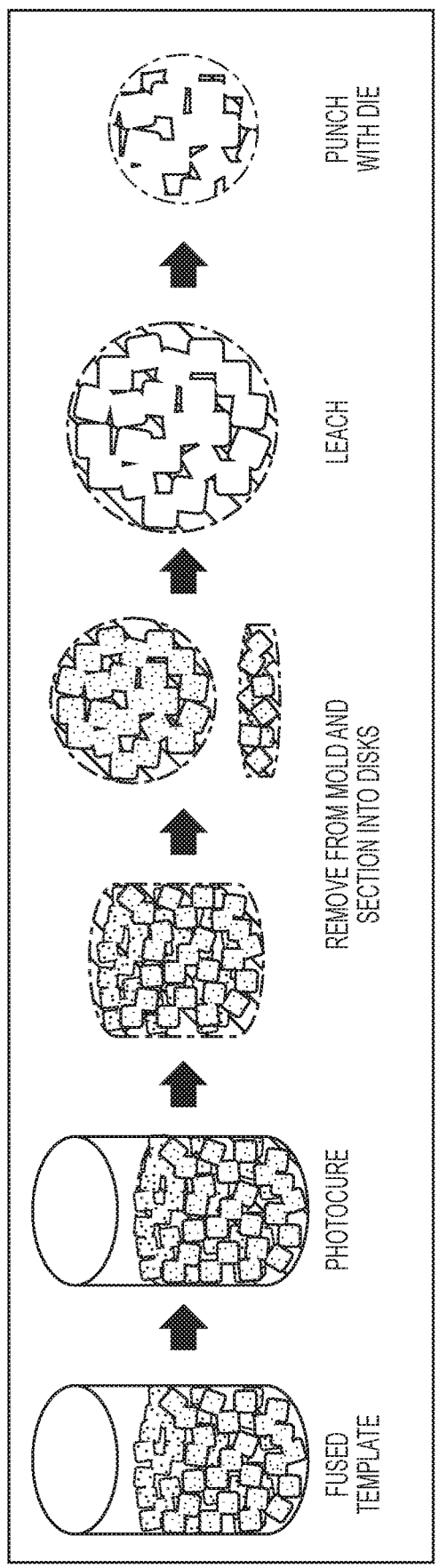
FIG. 4 shows the fabrication of macroporous PEG-DA hydrogels using a fused salt template and a solvent induced phase separation (SIPS).

FIG. 4 shows macroporous PEG-DA (diacrylated poly (ethylene glycol)) hydrogels that were fabricated using a fused salt template and a solvent induced phase separation (SIPS). Salt fusion was achieved by the addition of a small amount of water to the salt (5 wt %). A PEG-DA precursor solution (in DCM, dichloromethane) was cured around the fused template, sectioned into discs, and placed in water to allow for leaching of porogen and impurities.

One skilled in the art will appreciate that various polymers, macromers, monomers, crosslinkers and combinations may be used in preparation of the implant. Specific examples provided herein are examples only and should not be considered limiting.

WORKING EXAMPLES

In the following specific examples, inorganic, methacrylated star polydimethylsiloxane ($PDMS_{star}$-MA) and organic, diacrylated poly(ethylene glycol) (PEG-DA) are used to form the hydrogel implants. The $PDMS_{star}$-MA component is osteoinductive (i.e. stimulating differentiation of multipotent cells into bone-forming lineages) and bioactive (i.e. promoting integration/bonding with surrounding bone tissue and the attachment & differentiation of osteogenic cells). In these examples, 3 hydrogel zones, of roughly equal height, are produced for each implant. The implants are formed by sequentially curing each layer using UV light, with or without a salt poragen template, in a cylindrical glass mold of a certain diameter and height. In this way, a cylindrical implant is formed with the corresponding hydrogel zones. In each example, a photocatalyst, (for example, 30 weight % solution of DMAP (4-Dimethylamino pyridine) in NVP (N-Vinylpyrrolidone) is used to accelerate UV-cure.

Example 1: 3 Hydrogel Zones; all Non-porated

Water is used to form the precursor solutions. A salt template (i.e. poragen) is not used. The ratio of $PDMS_{star}$-MA:PEG-DA is systematically increased from the $1^{st}$ (bottom) to the $3^{rd}$ (top) hydrogel zone (i.e. a relative decrease in $PDMS_{star}$-MA from the bottom to top zone).

The $1^{st}$ (bottom) hydrogel zone is fabricated by the UV cure (30 sec) of a precursor solution layer comprised of a 20:80 weight % ratio of $PDMS_{star}$-MA to PEG-DA (10 weight % in water). Next, the $2^{nd}$ (middle) hydrogel zone is fabricated by the UV cure (30 sec) of a precursor solution layer comprised of a 10:90 weight % ratio of $PDMS_{star}$-MA to PEG-DA (10 weight % in water) added on top of the first hydrogel zone. The $3^{rd}$ (top) hydrogel zone is fabricated by the UV cure (30 sec) of a precursor solution layer comprised of a 0:100 weight % ratio of $PDMS_{star}$-MA to PEG-DA (10 weight % in water) added on top of the middle hydrogel zone. In a final step, the implant is then exposed to UV light for another 2 minutes.

Example 2: 3 Hydrogel Zones; Porated

Dichloromethane (DCM) is used to form the precursor solutions. A salt template is used in which average salt size decreases systematically from the $1^{st}$ (bottom) to $3^{rd}$ (top) hydrogel zone. The ratio of $PDMS_{star}$-MA:PEG-DA is systematically increased from the $1^{st}$ (bottom) to $3^{rd}$ (top) hydrogel zone. Lastly, the salt template is removed via leaching in water to produce the final implant.

For each hydrogel zone, a salt template (of a given hydrogel zone) is first created with the designated average salt size and fused with the addition of a small amount of water and optionally air dried. To this is added the designated precursor solution, the diffusion of which may be aided with centrifugation.

The $1^{st}$ (bottom) hydrogel zone is fabricated by the UV cure (30 sec) of a precursor solution layer comprised of a 20:80 weight % ratio of $PDMS_{star}$-MA to PEG-DA (10 weight % in DCM). Next, the $2^{nd}$ (middle) hydrogel zone is fabricated by the UV cure (30 sec) of a precursor solution layer comprised of a 10:90 weight % ratio of $PDMS_{star}$-MA to PEG-DA (10 weight % in DCM) added on top of the bottom hydrogel zone. The $3^{rd}$ (top) hydrogel zone is fabricated by the UV cure (30 sec) of a precursor solution layer comprised of a 0:100 weight % ratio of $PDMS_{star}$-MA to PEG-DA (10 weight % in DCM) added on top of the middle hydrogel zone. In a final step, the implant is then exposed to UV light for another 2 minutes.

Example 3: 3 Hydrogel Zones; 2 Porated and 1 Non-porated

Dichloromethane (DCM) is used to form the precursor solutions for the two porated hydrogel zones. A salt template is used in which average salt size varies systematically increased from the $1^{st}$ (bottom) to $2^{nd}$ (middle) hydrogel zone. For the $3^{rd}$ (top) hydrogel zone, water is used to form the precursor solution and a salt template is not used. The ratio of $PDMS_{star}$-MA:PEG-DA is systematically increased from the $1^{st}$ (bottom) to the $3^{rd}$ (top) hydrogel zone. Lastly, the salt template of the $1^{st}$ (bottom) and $2^{nd}$ (middle) is removed via leaching in water to produce the final implant.

For the $1^{st}$ (bottom) to $2^{nd}$ (middle) hydrogel zone, a salt template (of a given hydrogel zone) is first created with the designated average salt size and fused with the addition of a small amount of water (so as to barely wet the salt) and then air dried. To this is added the designated precursor solution, the diffusion of which may be aided with centrifugation.

The $1^{st}$ (bottom) hydrogel zone is fabricated by the UV cure (30 sec) of a precursor solution layer comprised of a 20:80 weight % ratio of $PDMS_{star}$-MA to PEG-DA (10 weight % in DCM). Next, the $2^{nd}$ (middle) hydrogel zone is fabricated by the UV cure (30 sec) of a precursor solution layer comprised of a 10:90 weight % ratio of $PDMS_{star}$-MA to PEG-DA (10 weight % in DCM) added on top of the $1^{st}$ hydrogel zone. After formation of the porated $1^{st}$ and $2^{nd}$ hydrogel zones, the salt is leached into an aqueous solution. Next, the cylinder is transferred into the cylindrical mold. The $3^{rd}$ (top) hydrogel zone is fabricated by the UV cure (30 sec) of a precursor solution layer comprised of a 0:100 weight % ratio of $PDMS_{star}$-MA to PEG-DA (10 wt % in water) added on top of the middle hydrogel zone. In a final step, the implant is then exposed to UV light for another 2 minutes.

While the present invention has been described in terms of certain preferred embodiments, it will be understood, of course, that the invention is not limited thereto since modifications may be made to those skilled in the art, particularly in light of the foregoing teachings.

What is claimed is:

1. A hydrogel implant comprising three or more hydrogel zones, wherein each hydrogel zone exhibits distinct tunable chemical and/or physical properties relative to one another and exhibits interpenetration between the adjacent hydrogel zones, and wherein the hydrogel zones comprise an inorganic polymer and an organic polymer wherein the inorganic polymer is methacrylated star polydimethylsiloxane and the organic polymer is diacrylated poly(ethylene glycol).

2. The hydrogel implant of claim 1, wherein the hydrogel implant is non-porated.

3. The hydrogel implant of claim 2, wherein a first hydrogel zone is fabricated from a first precursor solution comprising about 20:80 weight % ratio of inorganic polymer to organic polymer.

4. The hydrogel implant of claim 2, wherein a second hydrogel zone is fabricated from a second precursor solution comprising about 10:90 weight % ratio of inorganic polymer to organic polymer.

5. The hydrogel implant of claim 2, wherein a third hydrogel zone is fabricated from a third precursor solution comprising about 0:100 weight % ratio of inorganic polymer to organic polymer.

6. The hydrogel implant of claim 1, wherein the hydrogel implant is porated.

7. The hydrogel implant of claim 6, wherein a first hydrogel zone is fabricated from a first precursor solution comprising about 20:80 weight % ratio of inorganic polymer to organic polymer.

8. The hydrogel implant of claim 6, wherein a second hydrogel zone is fabricated from a second precursor solution comprising about 10:90 weight % ratio of inorganic polymer to organic polymer.

9. The hydrogel implant of claim 6, wherein a third hydrogel zone is fabricated from a third precursor solution comprising about 0:100 weight % ratio of inorganic polymer to organic polymer.

10. The hydrogel implant of claim 1, wherein the three or more hydrogel zones are at least one of discrete layers and continuous gradients of different compositions.

11. The hydrogel implant of claim 1, wherein at least one of the three or more hydrogel zones has a different porosity.

12. The hydrogel implant of claim 1, wherein the three or more hydrogel zones are a combination of non-porated and porated zones.

13. A method of preparing a hydrogel implant according to claim 1 comprising:
   preparing a first precursor solution comprised of about 20:80 weight % ratio of inorganic polymer to organic polymer;
   placing the first precursor solution layer within a cylindrical glass chamber;
   curing the first precursor solution layer to form a first hydrogel zone;
   preparing a second precursor solution comprised of a 10:90 weight % ratio of inorganic polymer to organic polymer 10 weight % in water;
   placing the second precursor solution layer within the cylindrical glass chamber over the first hydrogel zone;
   curing the second precursor solution layer to form a second hydrogel zone;
   preparing a third precursor solution comprised of a 0:100 weight % ratio of inorganic polymer to organic polymer;
   placing the third precursor solution layer within the cylindrical glass chamber over the first hydrogel zone; and
   curing the third precursor solution layer to form a third hydrogel zone, wherein the combination of the first hydrogel zone, the second hydrogel zone and the third hydrogel zone forms a hydrogel implant.

14. The method of claim 13, comprising adding additional hydrogel zones to the hydrogel implant by preparing additional precursor solutions, and sequentially placing the additional precursor solutions within the cylindrical glass chamber, over the top hydrogel zone of the hydrogel implant, and curing the additional precursor solution to form the additional hydrogel zone.

15. The method of claim 13, where the hydrogel implant is formed by placing the precursor solutions are cast over a poragen template placed within the cylindrical glass chamber, wherein the poragen template is comprised of salt, NaCl, $CaCl_2$, $RbCl_2$, paraffin, or sugar.

16. The method of claim 15, wherein the hydrogel implant is immersed in an aqueous solution to remove the poragen template prior to removing the hydrogel implant from the cylindrical glass chamber.

17. The method of claim 13, where each hydrogel zone is crosslinked to the adjacent hydrogel zone.

18. The method of claim 17, wherein the crosslinking is peformed using a chemical crosslinker.

19. The method of claim 17, wherein the crosslinking is performed using ultraviolet light.

20. A method for treating osteochondral defects in a subject, the method comprising: shaping the defect to accommodate a hydrogel implant according to claim 1 using arthroscopic techniques, implanting an autograft-sized, hydrogel implant, as determined by the arthroscopic technique used to shape the defect, providing structural support to the defect such that the hydrogel implant acts as support scaffolding and in the regeneration of the tissue types proximate to each hydrogel zone along the longitudinal axis of the hydrogel implant.

\* \* \* \* \*